(12) United States Patent
Rich

(10) Patent No.: US 7,403,125 B2
(45) Date of Patent: Jul. 22, 2008

(54) FLOW CYTOMETRY SYSTEM WITH BUBBLE DETECTION

(75) Inventor: Collin Rich, Ypsilanti, MI (US)

(73) Assignee: Accuri Cytometers, Inc., Ann Harbor, MI (US)

( * ) Notice: Subject to any disclaimer, the term of this patent is extended or adjusted under 35 U.S.C. 154(b) by 108 days.

(21) Appl. No.: 11/430,591

(22) Filed: May 8, 2006

(65) Prior Publication Data

US 2007/0257215 A1 Nov. 8, 2007

Related U.S. Application Data

(60) Provisional application No. 60/678,831, filed on May 6, 2005.

(51) Int. Cl.
  *G08B 21/00* (2006.01)
  *B65B 1/30* (2006.01)
  *B65B 31/00* (2006.01)
  *B67C 3/02* (2006.01)

(52) U.S. Cl. .......................... 340/603; 340/619; 141/94

(58) Field of Classification Search ................. 340/607, 340/608, 619, 632–634; 141/94–96
See application file for complete search history.

(56) References Cited

U.S. PATENT DOCUMENTS

| | | | |
|---|---|---|---|
| 4,112,735 A | 9/1978 | McKnight | |
| 4,138,879 A | 2/1979 | Liebermann | |
| 4,371,786 A | 2/1983 | Kramer | |
| 4,559,454 A | 12/1985 | Kramer | |
| 4,570,639 A * | 2/1986 | Miodownik | 600/531 |
| 4,691,829 A * | 9/1987 | Auer | 209/3.1 |
| 5,043,706 A | 8/1991 | Oliver | |
| 5,083,862 A | 1/1992 | Rusnak | |
| 5,466,946 A * | 11/1995 | Kleinschmitt et al. | 250/577 |
| 5,539,386 A * | 7/1996 | Elliott | 340/632 |
| 5,559,339 A * | 9/1996 | Domanik et al. | 250/573 |
| 5,616,124 A * | 4/1997 | Hague et al. | 604/65 |
| 5,960,129 A * | 9/1999 | Kleinschmitt | 385/12 |
| 6,427,521 B2 | 8/2002 | Jakkula et al. | |
| 6,568,271 B2 | 5/2003 | Shah et al. | |
| 6,694,799 B2 | 2/2004 | Small | |
| 6,872,180 B2 | 3/2005 | Reinhardt et al. | |
| 6,908,226 B2 | 6/2005 | Siddiqui et al. | |
| 6,912,904 B2 | 7/2005 | Storm, Jr. et al. | |
| 6,941,005 B2 | 9/2005 | Lary et al. | |
| 2003/0062314 A1 | 4/2003 | Davidson et al. | |
| 2003/0072549 A1 | 4/2003 | Facer et al. | |
| 2003/0202175 A1 | 10/2003 | Van den Engh et al. | |
| 2003/0211009 A1 | 11/2003 | Buchanan | |
| 2004/0112808 A1 | 6/2004 | Takagi et al. | |

(Continued)

*Primary Examiner*—George A Bugg
*Assistant Examiner*—Jennifer Mehmood
(74) *Attorney, Agent, or Firm*—Jeffrey Schox

(57) ABSTRACT

The flow cytometry system of the present invention includes a flow channel including an interrogation zone. A light source and a light detector are connected to the interrogation zone, such that a sample flowing through the interrogation zone can be optically analyzed through methods known in the art of flow cytometry. A bubble detector is connected to the flow channel. A controller is connected to the bubble detector and is adapted to perform a predetermined output in response to the detection of a bubble in the flow channel. The predetermined output may include alerting a user as to the presence of a bubble, flagging potentially corrupted data, and ceasing data collection until the interrogation zone is clear of bubbles.

19 Claims, 1 Drawing Sheet

U.S. PATENT DOCUMENTS

2004/0123645 A1 7/2004 Storm, Jr. et al.
2005/0195684 A1 9/2005 Mayer
2005/0252574 A1 11/2005 Khan et al.

* cited by examiner

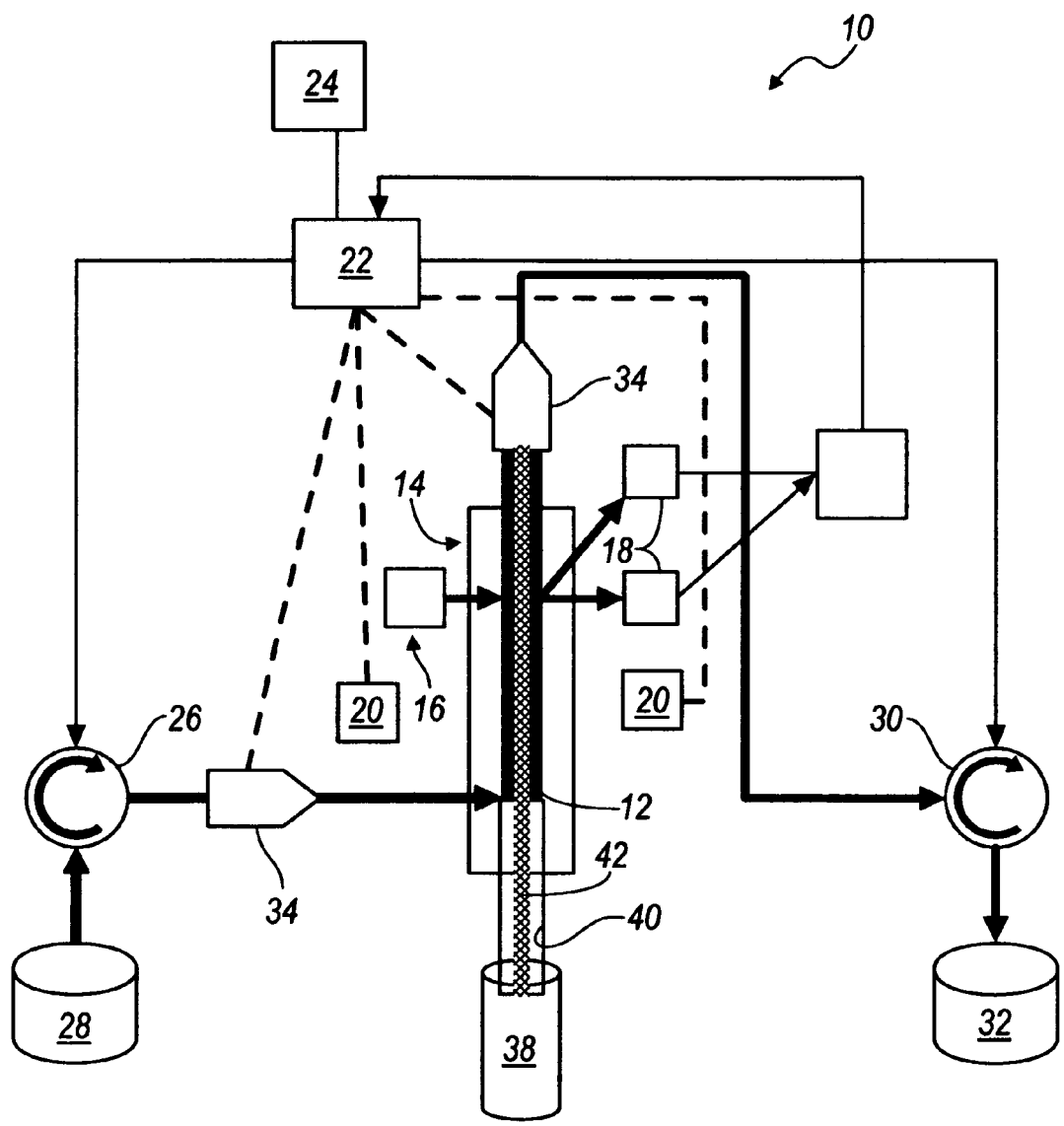
FIGURE

FLOW CYTOMETRY SYSTEM WITH BUBBLE DETECTION

CROSS-REFERENCE TO RELATED APPLICATIONS

This application claims the benefit of U.S Provisional Application number 60/678,831, filed May 6, 2005.

TECHNICAL FIELD

The present invention relates generally to the field of medical devices and more particularly to the field of flow cytometry.

BACKGROUND

The presence of bubbles in the flow cytometer system is one of the primary sources of corrupted experimental data. Typical flow cytometers periodically experience bubbles in the sheath fluid or sample fluid lines. Bubbles may be introduced externally from leaks in the flow line or a depleted sheath container or sample, or they may be generated internally from the coalescence or nucleation of gases dissolved in the sheath and/or sample fluids. Bubbles can cause anomalies in the flow within the flow cytometer system that reduce the performance of the flow cytometer. Furthermore, bubbles passing through the interrogation zone of the flow cytometer can cause spurious or false event signals that corrupt the experimental data being collected. The user can take corrective action only after the bubbles have been detected, which often occurs after experimental data has been corrupted and the user has been inconvenienced.

Thus, there is a need for a flow cytometry system that allows corrective actions to be taken before the experimental data is corrupted and the user is inconvenienced. This invention provides such an improved and useful flow cytometry system having bubble detection capabilities and automated controls for mitigating the effects of bubbles in the interrogation zone.

BRIEF DESCRIPTION OF THE FIGURE

The FIGURE is a schematic diagram of a flow cytometry system with bubble detection in accordance with the present invention.

DESCRIPTION OF THE PREFERRED EMBODIMENT

The following description of the preferred embodiment of the invention is not intended to limit the invention to this preferred embodiment, but rather to enable any person skilled in the art of flow cytometry to make and use this invention.

As shown in the FIGURE, the flow cytometry system 10 of the preferred embodiment includes a flow channel 12 defining an interrogation zone 14. A light source 16 and a light detector 18 are connected to the interrogation zone 14, such that a sample flowing through the interrogation zone 14 can be optically analyzed through methods known in the art of flow cytometry. A bubble detector 20 is connected to the flow channel 12. A controller 22 is connected to the bubble detector and is adapted to perform a predetermined output in response to the detection of a bubble in the flow channel 12.

The flow channel 12 of the preferred embodiment is connected to a sample container 38 by a drawtube 40. The flow channel 12 functions to contain and direct a sample fluid 42 through the interrogation zone 14 such that it can be analyzed. The drawtube 40 functions as a passageway into which the sample fluid 42 is drawn and transported to the flow channel 12. The sample fluid 42 may be anything capable of being inserted into the flow path. Samples within the sample fluid 42 may include cells, biological materials, or other particles to be assayed, measured, or counted. The interrogation zone 14 is a portion of the flow channel 12 that readily permits analysis of the sample fluid 42. In particular, the interrogation zone 14 is preferably transparent to the light source 16 and any range of light that may be scattered from the samples to the light detector 18.

The light source 16 and the light detector 18 of the preferred embodiment are connected to the interrogation zone 14. The light source 16 functions to emit a collimated beam of light, such as a laser beam, into the interrogation zone 14 from where it is scattered, absorbed, reflected, refracted, fluoresced, or transmitted by the sample within the sample fluid 42. The light detector 18 functions to collect the light that is scattered, absorbed, reflected, refracted, fluoresced, or transmitted by the sample within the sample fluid 42. Preferably, the light source 16 and the light detector 18 are connected to the controller 22, which is adapted to control the emissions of the light source 16 and receive detected signals from the light detector 18. Alternatively, there may be more than one light source 16 and more than one light detector 18, each of which may emit a distinct frequency band or be responsive to a distinct frequency band, respectively. The light source and the light detector may, however, be any suitable combination of suitable devices to facilitate the analysis of the sample.

The bubble detector 20 of the preferred embodiment is connected to the flow channel 12. The bubble detector 20 functions to detect the presence of one or more bubbles within the flow channel 12. Bubbles include one or more pockets of gas (such as air) in a fluid, such as the sample fluid 42. Bubbles may be of any size and may be present at any location in the fluid stream of the flow path, including in the flow channel 12 and the drawtube 40. The term bubbles as is used herein also includes continuous air entering the drawtube, which may occur as a result of an empty sample well or container. Bubbles may be moving or may be generally fixed within the flow channel 12, and they may be introduced externally (e.g. from leaks in the flow line, a sheath fluid container 28, or the sample container 38) or they may be generated internally (e.g., from the coalescence or nucleation of gases dissolved in the sheath fluid and/or sample fluid 42). The bubble detector 20 of the preferred embodiment may be an impedance detector, an electromagnetic detector, a capacitance detector, an ultrasound detector, or any other suitable bubble detector.

An impedance detector functions to detect the presence of a bubble in the flow channel 12 by measuring a change between the impedance of a fluid and the impedance of a fluid with a gas that forms a bubble. The impedance detector includes a transmitter and a receiver. The transmitter and the receiver are preferably electric devices and the signal acquired and analyzed by the receiver is preferably an electrical impedance. The transmitter is preferably any suitable emitter of an electric current (such as a first gold-plated electrode), and the receiver is preferably any suitable acquirer of the electric current (such as a second gold-plated electrode). Bubbles in fluid typically have higher electrical impedance than the fluid itself, particularly if the fluid contains conductive ions (which is typical of common flow cytometry buffers and samples). As such, the electrical impedance measured by the receiver will be modified when bubbles are present in the fluid stream between the transmitter and the receiver. Any suitable method may be used by the receiver to analyze whether the electrical impedance has been modified by the presence of bubbles in the fluid stream. Examples of suitable analysis methods include employing electrical impedance detection thresholds and/or algorithms that discriminate between the electrical impedance measurement of a fluid stream lacking bubbles and the electrical impedance measurement of a fluid stream containing bubbles. Electrical impedance measurements may be discriminated based on simple threshold or more complex pattern recognition algorithms. The analysis method used by the receiver may be preset, user defined, or dynamically created or altered.

An electromagnetic detector functions to detect the presence of a bubble in the flow channel 12 by measuring a difference in the electromagnetic properties of the fluid within the flow channel 12 as compared to the electromagnetic properties of the fluid with a gaseous bubble. The electromagnetic detector includes a transmitter and a receiver. The transmitter and receiver are optoelectronic devices and the signal acquired and measured by the receiver is an optical signal. The transmitter is preferably any suitable emitter of an electromagnetic wave (such as a light emitting diode), and the receiver is preferably any suitable acquirer of the electromagnetic wave (such as a photodetector). Bubbles in fluid typically cause the optical properties of the fluid, such as transmission, reflection, refraction, absorption and the like, to be altered. As such, the optical properties measured by the receiver will be modified when bubbles are present in the fluid stream between the transmitter and the receiver. Any suitable method may be used by the receiver to analyze whether the optical properties have been modified by the presence of bubbles in the fluid stream. Examples of suitable analysis methods include employing electromagnetic radiation detection thresholds and/or algorithms that discriminate between the intensity or frequency of light passing through a fluid stream lacking bubbles and the intensity or frequency measurement of a fluid stream containing bubbles. Optical property measurements may be discriminated based on a simple threshold or more complex pattern recognition algorithms. The analysis method used by the receiver may be preset, user defined, or dynamically created or altered. Furthermore, a "reference cell" of known configuration (e.g. a section of fluid flow path either free of bubbles or known to contain one or more bubbles) may be included in the system to provide a reference for threshold or other such parameters that enables compensation for dynamic changes in fluid composition, temperature, and the like.

A capacitance detector functions to detect the presence of a bubble in the flow channel 12 by measuring a difference in capacitance between a fluid passing through the flow channel 12 and a fluid having bubbles passing through the flow channel 12. The capacitance detector includes a transmitter and a receiver. The transmitter is preferably any suitable conductor of an electric current (such as a first gold-plated electrode), and the receiver is preferably any suitable conductor of the electric current (such as a second gold-plated electrode). The detector may further include an amplifier, diode, or other suitable electronic device for measuring a change in current in the conductor of the receiver. Bubbles in fluid typically have a lower dielectric constant than the fluid itself, particularly if the fluid contains conductive ions (which is typical of common flow cytometry buffers and samples). As such, the capacitance measured by the receiver will be modified when bubbles are present in the fluid stream between the transmitter and the receiver. Any suitable method may be used by the receiver to analyze whether the capacitance has been modified by the presence of bubbles in the fluid stream. Examples of suitable analysis methods include employing electrical current thresholds and/or algorithms that discriminate between the capacitance measurement of a fluid stream lacking bubbles and the capacitance measurement of a fluid stream containing bubbles. Capacitance measurements may be discriminated based on a simple threshold or more complex pattern recognition algorithms. The analysis method used by the receiver may be preset, user defined, or dynamically created or altered.

The ultrasound detector functions to detect the presence of a bubble in the flow channel 12 by measuring a difference in the acoustic properties of the fluid as compared to the acoustic properties of a fluid having one or more bubbles. The ultrasound detector includes a transmitter and a receiver. The transmitter is preferably any suitable emitter of an acoustic signal, and the receiver is preferably any suitable acquirer of the acoustic signal. Bubbles in fluid typically cause echoes, distortion or other measurable changes to the acoustic properties of the fluid. As such, the acoustic signal measured by the receiver will be modified when bubbles are present in the fluid stream between the transmitter and the receiver. Any suitable method may be used by the receiver to analyze whether the acoustic signal has been modified by the presence of bubbles in the fluid stream. Examples of suitable analysis methods include employing acoustic signal detection thresholds and/or algorithms that discriminate between the acoustic properties measurement of a fluid stream lacking bubbles and the acoustic properties measurement of a fluid stream containing bubbles. Acoustic signal measurements may be discriminated based on a simple threshold or more complex pattern recognition algorithms. The analysis method used by the receiver may be preset, user defined, or dynamically created or altered.

In a preferred embodiment, a single signal type is employed. In an alternative embodiment, a plurality of signal types emitted from one or more transmitters may be used. In alternative variations of the preferred embodiment, signal types other than electrical impedance, electromagnetic waves, capacitance and acoustic waves may be used. For the impedance detector, the electromagnetic detector, the capacitance detector, and the ultrasound detector, the transmitter and receiver may be connected to the system 10 in any configuration suitable for emitting and acquiring, respectively, a signal capable of being modified by the presence of bubbles. The receiver of the bubble detector 20 is preferably connected to the system 10 in relative close proximity to the transmitter (e.g. on opposite walls of the flow channel 12 such that the distance between the transmitter and receiver is approximately equal to the diameter of the flow channel 12). By placing the transmitter and receiver in close proximity to one another, the system 10 can identify the presence of bubbles at a relatively localized site along the flow path. Alternatively, the receiver may be connected to the system 10 along the flow path at a more distant location relative to the transmitter, which allows the system 10 to identify the presence of bubbles present along a length of the flow path, i.e. over a length of the flow channel 12. The signal emitted from the transmitter may be optimally adjusted to function with the particular configuration of the transmitter and receiver. In the preferred embodiment, a single transmitter and a single receiver are connected to the flow cytometer. In an alternative embodiment, a plurality of transmitters and receivers may be connected, thus permitting both localized and wide-area detection of bubbles. Any suitable combination of transmitters and receivers (either in a 1:1 ratio or any other suitable ratio) may be used.

In an alternative embodiment, the bubble detector 20 includes a data analysis unit connected to the light detector and adapted to detect the presence of a bubble in the interrogation zone. The data analysis unit may be connected to the interrogation zone 14, or alternatively, the data analysis unit may be integrated within the controller 22. The preferred data analysis unit functions to detect the presence of a bubble in the interrogation zone 14 by comparing the data received by the light detector 18 with a control data set that is indicative of a fluid without bubbles. The control data set may be programmed into the data analysis unit, it may be determined by a user, or alternatively it may be acquired by the data acquisition unit in real-time such that for each sample being analyzed, the data analysis unit includes a relevant control data set for comparison. Examples of suitable data discrimination analysis methods include signal detection thresholds and/or algorithms that discriminate between the measured properties of a fluid lacking bubbles and the properties measured of a fluid containing bubbles. Signal measurements may be discriminated based on a simple threshold or more complex pattern recognition algorithms. The analysis method used by the data analysis unit may be preset, user defined, or dynamically created or altered.

Once the bubble detector 20 has detected bubbles, the system 10 preferably implements or suggests corrective actions to avoid or limit the corruption of the experimental data and/or inconvenience to the user. Preferably, the controller 22 is adapted to perform a predetermined output in response to the detection of a bubble. In a first variation of the controller 22, the predetermined output includes alerting a user regarding the detection of a bubble. To alert the user, the system 10 preferably includes a user interface 24 that is connected to the controller 22. The user interface 24 may include a display and/or speakers that enable the controller to initiate a visual and/or audio alert to the user in response to the detection of a bubble. For example, a display on the user interface 24 may visually indicate the detection of a bubble through those means and methods known in the communications arts. The system 10 may, however, alternatively include any other suitable method or device to alert the user regarding the detection of a bubble.

In a second variation of the controller 22, the predetermined output performed includes flagging data. In response to the detection of a bubble, the controller 22 is adapted to flag data, recognizing that the data may be corrupted, inaccurate, or otherwise unreliable. Preferably, the controller 22 flags the data in the time domain, independently of the quality, quantity, or other characteristics of the data received from the interrogation zone 14. That is, the controller 22 is adapted to associate a time with the detection of a bubble, through an internal clock or other mechanism, and flag the data associated with the time at which the bubble was detected by the bubble detector 20. Preferably, the controller flags the data in the time domain for an interval of time that substantially corresponds to the detection of a bubble in the interrogation zone. As such, if a single bubble is detected as it passes through the interrogation zone, then the interval of time would be the amount of time that it took the bubble to exit the interrogation zone after detection. Alternatively, the interval of time may automatically include a predetermined amount of time prior to the detection of the bubble, thus accounting for any delay or error in the bubble detection process or the transmission of the detection signal to the controller 22 from the bubble detector 20. The interval of time may also be fixed, based upon historical or estimated time intervals for clearing the interrogation zone 14 of bubbles, or user defined prior to experimentation or during the experiment based upon the observations of the user of the data stream.

In a third variation of the controller 22, the predetermined output includes ceasing data collection in response to the detection of a bubble. The cessation of data collection can be accomplished through control of the light source 16 and the light detector 18, both of which are connected to the controller 22. In response to the detection of a bubble, the controller 22 preferably ceases, or otherwise modifies, the operation of the light source 16 and/or the light detector 18, thus preventing the acquisition of corrupted or otherwise unusable data from the interrogation zone 14. When the flow channel 12 is clear of bubbles, the controller 22 preferably resumes normal operation of the light source 16 and/or light detector 18 in accordance with the standard operation of the flow cytometry system 10.

The system 10 of the preferred embodiment also includes a sheath fluid pump 26, which is in fluid communication with the flow channel 12. The sheath fluid pump 26 functions to pump sheath fluid from a sheath fluid container 28 into the flow channel 12. The sheath fluid functions to hydrodynamically focus the sample fluid 42, and the sample located therein, as it passes through the interrogation zone. The sheath fluid may be distilled water or phosphate-buffered saline, or any other suitable fluid for hydrodynamically focusing the sample in the interrogation zone 14. The system 10 of the preferred embodiment also includes a waste fluid pump 30, which is in fluid communication with the flow channel 12. The waste fluid pump 30 functions to extract waste fluid (the mixture of the sheath fluid and the sample fluid 42) from the flow channel 12 and deposit the waste fluid into a waste fluid container 32.

The preferred controller 22 controls the flow rate of both the sheath fluid pump 26 and the waste fluid pump 30. In operation, the sheath fluid pump 26 and the waste fluid pump 30 preferably cooperate to draw the sample fluid 42 from the sample container 38 into the interrogation zone 14 through the use of a pressure differential (e.g., the sheath fluid pump 26 "pushes" the sheath fluid and the waste fluid pump 30 "pulls" the sheath fluid and the sample fluid 42). In order to allow a variable flow rate of the sample fluid 42, the system 10 preferably allows for a variable flow rate of the sheath fluid and/or the waste fluid. For example, the sheath fluid pump 26 and the waste fluid pump 30 may be driven by a single motor with a variable drive ratio device (e.g., transmission), by a single motor with at least one valve 34 (such as a by-pass valve or restrictive valve) located near the sheath fluid pump 26 and/or the waste fluid pump 30 to divert or restrict a variable amount of the fluid flow, by separate motors with separate controls, or by any other suitable method or device such as the control schemes taught in U.S. patent application Ser. No. 11/370,714 filed 8 Mar. 2006 and entitled "Fluidic System For A Flow Cytometer", which is incorporated in its entirety by this reference. As such, the controller 22 may cease data collection through control the flow of sample fluid 42 through the flow channel 12 through control of the sheath fluid pump 26 and/or the waste fluid pump 30.

In response to the detection of a bubble, the controller 22 may be adapted to vary the flow rates of the sheath fluid pump 26 and the waste fluid pump 30 such that their respective flow rates are substantially identical. As previously noted, the sample fluid 42 is pulled into the flow channel 12 by the pressure differential generated by the sheath fluid pump 26 and the waste fluid pump 30. Therefore, if the controller 22 operates the sheath fluid pump 26 and the waste fluid pump 30 at identical or substantially identical flow rates, then no sample fluid 42 will be injected into the flow channel 42. As such, the sample fluid 42 and the sample will be conserved, the bubble will pass through the interrogation zone 14, and data collection will effectively cease as no new samples will enter into the interrogation zone. When the flow channel 12 is clear of bubbles, the controller 22 preferably returns the flow rate of the sheath fluid pump 26 and the waste fluid pump 30 to their respective normal operational flow rates and normal analysis of the sample fluid 42 may resume.

Alternatively, in response to the detection of a bubble, the controller 22 may be adapted to dynamically vary the flow rates of the sheath fluid pump 26 and the waste fluid pump 30. For example, in response to the detection of a bubble, the controller may alternately increase the flow rate of the waste fluid pump 30 and decrease the rate of the sheath fluid pump 26, resulting in a harmonic pressure differential within the system 10 that dissipates, destroys or otherwise removes the bubbles from the interrogation zone 14. The controller 22 may be adapted to dynamically vary the flow rates of the sheath fluid pump 26 and the waste fluid pump 30 at constant or variable frequencies between one and one hundred Hz in order to remove the bubbles from the interrogation zone 42. Once the bubble detector 20 indicates that the interrogation zone 14 is clear of bubbles, then the controller 22 may be adapted to return the flow rate of the sheath fluid pump 26 and the waste fluid pump 30 to their respective normal operational flow rates and normal analysis of the sample fluid 42 may resume.

In addition to controlling the flow rates of the sheath fluid pump 26 and the waste fluid pump 30, the controller 22 may also be adapted to control the valve 34 in fluid communication with the interrogation zone 14. For example, the controller 22 may control the flow rate of the sheath fluid and/or the waste fluid by controlling a by-pass valve or a restrictive valve. As previously noted, by controlling the flow rate of the sheath fluid and/or the waste fluid, the controller 22 can cease data collection while removing bubbles from the interrogation zone. Control of the flow rates of the sheath fluid and/or waste fluid may accelerate the removal of bubbles from the flow channel 12. Alternatively, control of the flow rates of the sheath fluid and/or waste fluid may cause harmonic pressure differentials that dissipate, destroy or otherwise remove the bubbles from the interrogation zone. Alternatively, control of the flow rates of the sheath fluid and/or waste fluid may cause a pressure equilibrium that results in the cessation of sample fluid 42 being pulled into the flow channel 12. Once the bubble detector 20 indicates that the interrogation zone 14 is clear of bubbles, then the controller 22 may be adapted to return the valve 34 to its respective normal operational levels and normal analysis of the sample fluid 42 may resume.

As a person skilled in the art of flow cytometry will recognize from the previous detailed description and from the figure and claims, modifications and changes can be made to the preferred embodiment of the invention without departing from the scope of this invention defined in the following claims.

I claim:

1. A flow cytometry system for collecting data on a sample fluid, comprising:
    a flow channel adapted to contain and direct a sample fluid, the flow channel defining an interrogation zone;
    a light source connected to the interrogation zone and adapted to emit light toward the sample fluid in the interrogation zone;
    a light detector connected to the interrogation zone and adapted to collect light from the interrogation zone and to provide collection data based on the collected light;
    a bubble detector coupled to the flow channel and adapted to detect the presence of a bubble in the flow channel; and
    a controller connected to the light detector and to the bubble detector and adapted to flag data within the collection data provided by the light detector during the detection of a bubble in the flow channel by the bubble detector.

2. The system of claim 1 wherein the bubble detector includes one of an impedance detector, an electromagnetic detector, a capacitance detector, or an ultrasound detector.

3. The system of claim 1 wherein the bubble detector includes a capacitance detector.

4. The system of claim 1 wherein the bubble detector includes a data analysis unit connected to the light detector and adapted to detect the presence of a bubble in the interrogation zone of the flow channel.

5. The system of claim 1 wherein the controller is adapted to alert a user in response to the detection of a bubble in the flow channel.

6. The system of claim 5 wherein the controller is further adapted to visually alert a user in response to the detection of a bubble in the flow channel.

7. The system of claim 1 wherein the controller is further adapted to flag data from the light detector in a time domain.

8. The system of claim 7 wherein the controller is further adapted to flag data over an interval of time in the time domain that substantially corresponds to the detection of a bubble in the flow channel.

9. flow cytometry system for collecting data on a sample fluid, comprising:
    a flow channel adapted to contain and direct a sample fluid, the flow channel defining an interrogation zone;
    a light source connected to the interrogation zone and adapted to emit light toward the sample fluid in the interrogation zone;
    a light detector connected to the interrogation zone and adapted to collect light from the interrogation zone;
    a bubble detector coupled to the flow channel and adapted to detect the presence of a bubble in the flow channel; and
    a controller connected to the bubble detector and adapted to cease data collection by controlling the light source and the light detector.

10. The system of claim 9 wherein the bubble detector includes a capacitance detector.

11. The system of claim 9 wherein the bubble detector includes a data analysis unit connected to the light detector and adapted to detect the presence of a bubble in the interrogation zone of the flow channel.

12. The system of claim 9 wherein the controller is adapted to alert a user in response to the detection of a bubble in the flow channel.

13. A flow cytometry system for collecting data on a sample fluid, comprising:
    a flow channel adapted to contain and direct a sample fluid, the flow channel defining an interrogation zone;
    a bubble detector coupled to the flow channel and adapted to detect the presence of a bubble in the flow channel;
    a sheath fluid pump adapted to pump sheath fluid from a sheath fluid container into the flow channel; and
    a controller connected to the bubble detector and adapted to cease data collection by controlling the sheath fluid pump.

14. The system of claim 13 further comprising a waste fluid pump adapted to extract waste fluid from the flow channel into a waste fluid container, wherein the controller is further adapted to cease data collection by controlling the waste fluid pump.

15. The system of claim 14 wherein the controller is further adapted to cease data collection by controlling a sheath fluid pump and a waste fluid pump such that the flow rate of the sheath fluid pump is substantially identical to the flow rate of the waste fluid pump.

16. The system of claim 13 further comprising a valve in fluid communication with the flow channel, wherein the controller is further adapted to cease data collection by controlling the valve.

17. The system of claim 13 wherein the bubble detector includes a capacitance detector.

18. The system of claim 13 further comprising:
a light source connected to the interrogation zone and adapted to emit light toward the sample fluid in the interrogation zone; and
a light detector connected to the interrogation zone and adapted to collect light from the interrogation zone;
wherein the bubble detector includes a data analysis unit connected to the light detector and adapted to detect the presence of a bubble in the interrogation zone of the flow channel.

19. The system of claim 13 wherein the controller is adapted to alert a user in response to the detection of a bubble in the flow channel.

* * * * *

UNITED STATES PATENT AND TRADEMARK OFFICE
CERTIFICATE OF CORRECTION

PATENT NO.        : 7,403,125 B2
APPLICATION NO.   : 11/430591
DATED             : July 22, 2008
INVENTOR(S)       : Collin Rich It is certified that error appears in the above-identified patent and that said Letters Patent is hereby corrected as shown below:

In column 8, line 30, the part of the sentence "9. flow cytometry system for collecting data on a sample" should read --9. A flow cytometry system for collecting data on a sample--

Signed and Sealed this

Twenty-third Day of September, 2008

JON W. DUDAS
*Director of the United States Patent and Trademark Office*